United States Patent [19]
Shoemaker, II

[11] Patent Number: 5,974,344
[45] Date of Patent: Oct. 26, 1999

[54] WOUND CARE ELECTRODE

[76] Inventor: Charles Shoemaker, II, 2404 W. 2nd St., Apartment A, Monahans, Tex. 79756

[21] Appl. No.: 09/032,792

[22] Filed: Mar. 2, 1998

[51] Int. Cl.[6] .................................................. A61N 1/04
[52] U.S. Cl. .................................... 607/149; 607/152
[58] Field of Search .................................. 607/149, 152, 607/153

[56] References Cited

U.S. PATENT DOCUMENTS

| | | |
|---|---|---|
| D. 327,739 | 7/1992 | Anderson . |
| 4,155,354 | 5/1979 | Rasmussen . |
| 4,699,146 | 10/1987 | Sieverding ............................. 607/152 |
| 4,736,752 | 4/1988 | Munck et al. . |
| 4,817,594 | 4/1989 | Juhasz .................................... 607/152 |
| 4,934,383 | 6/1990 | Glumac .................................. 607/152 |
| 5,038,796 | 8/1991 | Axelgaard et al. . |
| 5,205,297 | 4/1993 | Montecalvo et al. . |
| 5,218,973 | 6/1993 | Weaver et al. ......................... 607/152 |
| 5,263,481 | 11/1993 | Axelgaard . |
| 5,848,966 | 12/1998 | Gusakov et al. ....................... 607/152 |

FOREIGN PATENT DOCUMENTS

| | | |
|---|---|---|
| 9105509 | 5/1991 | WIPO . |
| 9309713 | 5/1993 | WIPO . |

OTHER PUBLICATIONS

Product Advertisement for Skinease Sticky Dots Electrode, Sterling Medical Technologies, Inc., Published priort to May 15, 1997.

*Primary Examiner*—Lee Cohen
*Attorney, Agent, or Firm*—Stephen R. Greiner

[57] ABSTRACT

A wound care electrode including a flexible, electrically conductive body and an electrically conductive gel layer secured to the bottom of the electrically conductive body for releasably coupling the electrically conductive body with the skin of a user. A flexible, nonconductive, separating layer is secured to the top of the electrically conductive body. A flexible, absorbent dressing is secured to the top of the separating layer. The electrically conductive body, the electrically conductive gel layer, and the separating layer have axially aligned perforations for conveying seepage from the skin of a user to the absorbent dressing.

17 Claims, 2 Drawing Sheets

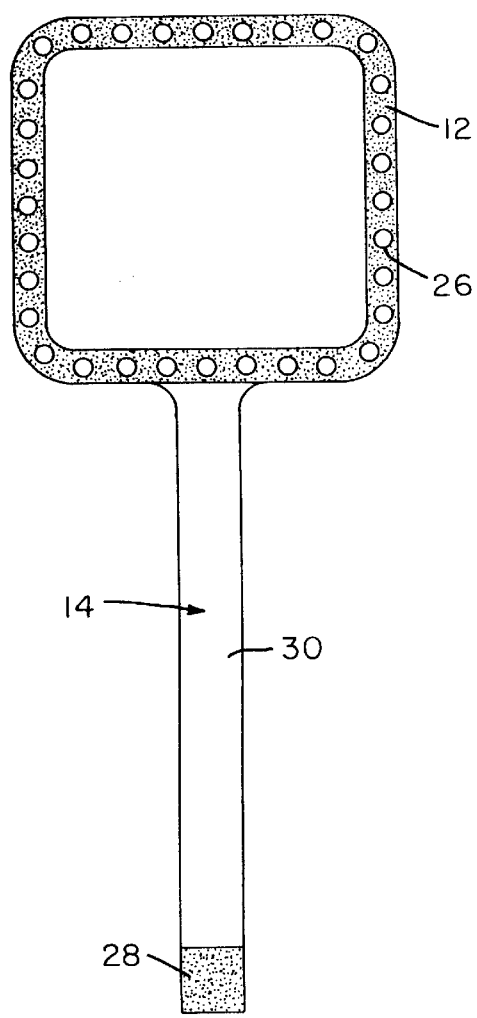
FIG. 3
FIG. 4
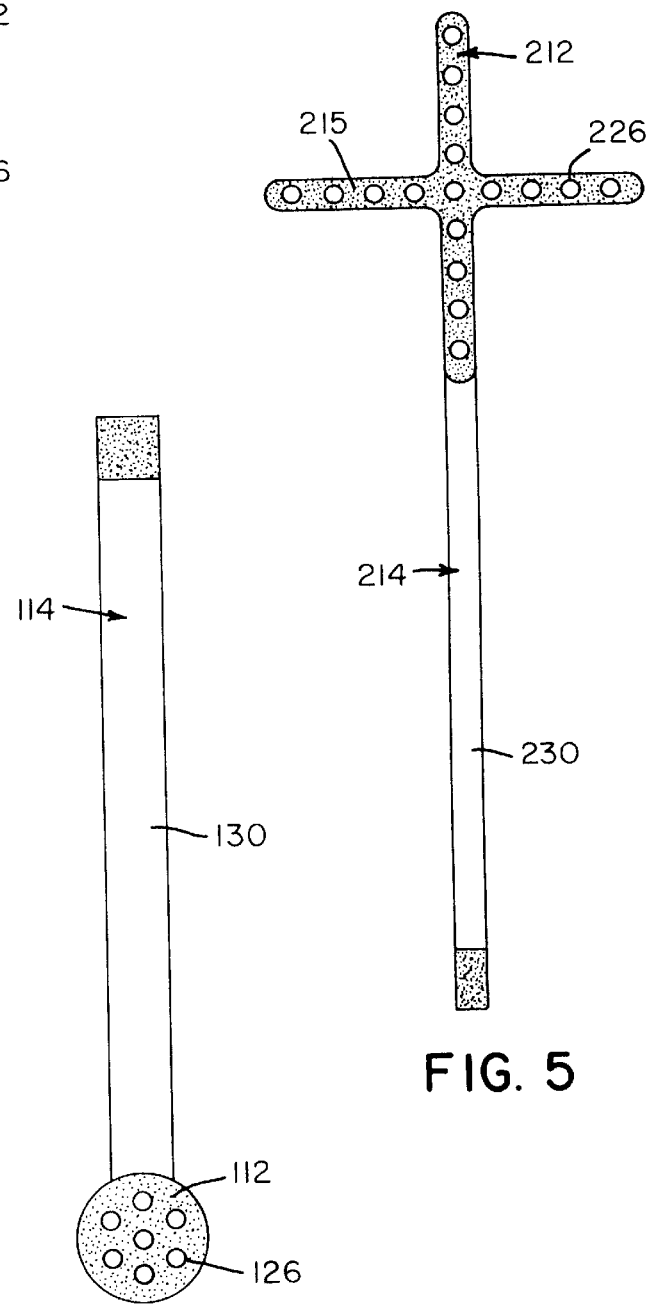
FIG. 5

WOUND CARE ELECTRODE

FIELD OF THE INVENTION

The present invention relates generally to surgical apparatus and, in particular, to an electrode for adhesive mounting on a body.

BACKGROUND OF THE INVENTION

It is generally accepted that health benefits can be obtained by delivering direct electrical current to wounds in the skin caused by disease or trauma. Tests have shown that the application of a positively charged electrode to a wound will: reduce the flow of blood to the wound, minimize bleeding, attract oxygen, speed healing, and prevent the swelling of tissue adjacent the wound. The application of a negatively charged electrode to a wound, on the other hand, will increase blood flow to the wound thereby killing germs at an increased rate and minimizing the likelihood of prolonged tissue swelling.

A basic treatment protocol is for the direct electrical current to be applied to a wound for one hour two times per day. An "application" electrode of appropriate polarity is first placed over the wound after it has been packed with a conductive medium such as saline-soaked gauze. Next, a "dispersive" electrode, having a polarity opposite that of the application electrode, is secured to the skin a short distance away from the wound. Then, electric current from a remote source is flowed between the application and dispersive electrodes.

While skin-contacting electrodes of the type described are widely known, they tend to possess shortcomings which have limited their use. First, the known electrodes are generally bulky making them uncomfortable and difficult to position adjacent many wounds (especially those located under plaster casts or other orthotic devices). Second, the use of saline-soaked gauze as a conductive medium between the electrodes and the skin can macerate healthy tissue after prolonged use and deposit unwanted fibers in wounds. Finally, the known electrodes are limited in their ability to draw wound seepage from the skin thus requiring their frequent movement for wound cleaning purposes.

SUMMARY OF THE INVENTION

In light of the problems associated with the known skin-contacting electrodes, it is a principal object of the invention to provide a wound care electrode which is thin, flexible and somewhat resilient. Thus, the electrode in accordance with this invention may be readily and comfortably positioned: within orthotic devices, under compression garments such as Ace bandages, and upon curved skin surfaces as needed.

It is another object of the invention to provide a wound care electrode of the type described which is self-adhering to a wound for use yet is easily releasable therefrom when use is discontinued.

It is a further object of the invention to provide a wound care electrode of the type described which draws wound seepage away from the skin of a user to reduce the opportunity for infection and to permit the electrode to be left in place for extended periods of use.

Still another object of the invention is to provide a would care electrode which is simple to use and may be employed by a novice for therapeutic purposes after minimal training and with minimal supervision.

It is an object of the invention to provide improved elements and arrangements thereof in a wound care electrode for the purposes described which is lightweight in construction, inexpensive in manufacture, and fully effective in use.

Briefly, the wound care electrode in accordance with this invention achieves the intended objects by featuring a flexible, electrically conductive body and an electrically conductive, hydrogel layer secured to the bottom thereof for releasably coupling the electrically conductive body with the skin of a user. A flexible, nonconductive, separating layer is secured to the top of the electrically conductive body. A flexible, absorbent dressing is secured to the top of the separating layer. The electrically conductive body, the hydrogel layer, and the separating layer have axially aligned perforations for conveying seepage from the skin of a user to the absorbent dressing.

The foregoing and other objects, features and advantages of the present invention will become readily apparent upon further review of the following detailed description of the preferred embodiments as illustrated in the accompanying drawings.

BRIEF DESCRIPTION OF THE DRAWINGS

The present invention may be more readily described with reference to the accompanying drawings, in which:

FIG. 3 is a top plan view of the flexible, conductive body employed in the wound care electrode of FIG. 1.

FIG. 4 is a top plan view of a first alternative, flexible, conductive body.

FIG. 5 is a top plan view of a second alternative, flexible, conductive body.

Similar reference characters denote corresponding features consistently throughout the accompanying drawings.

DETAILED DESCRIPTION OF THE PREFERRED EMBODIMENTS

Figure 1:
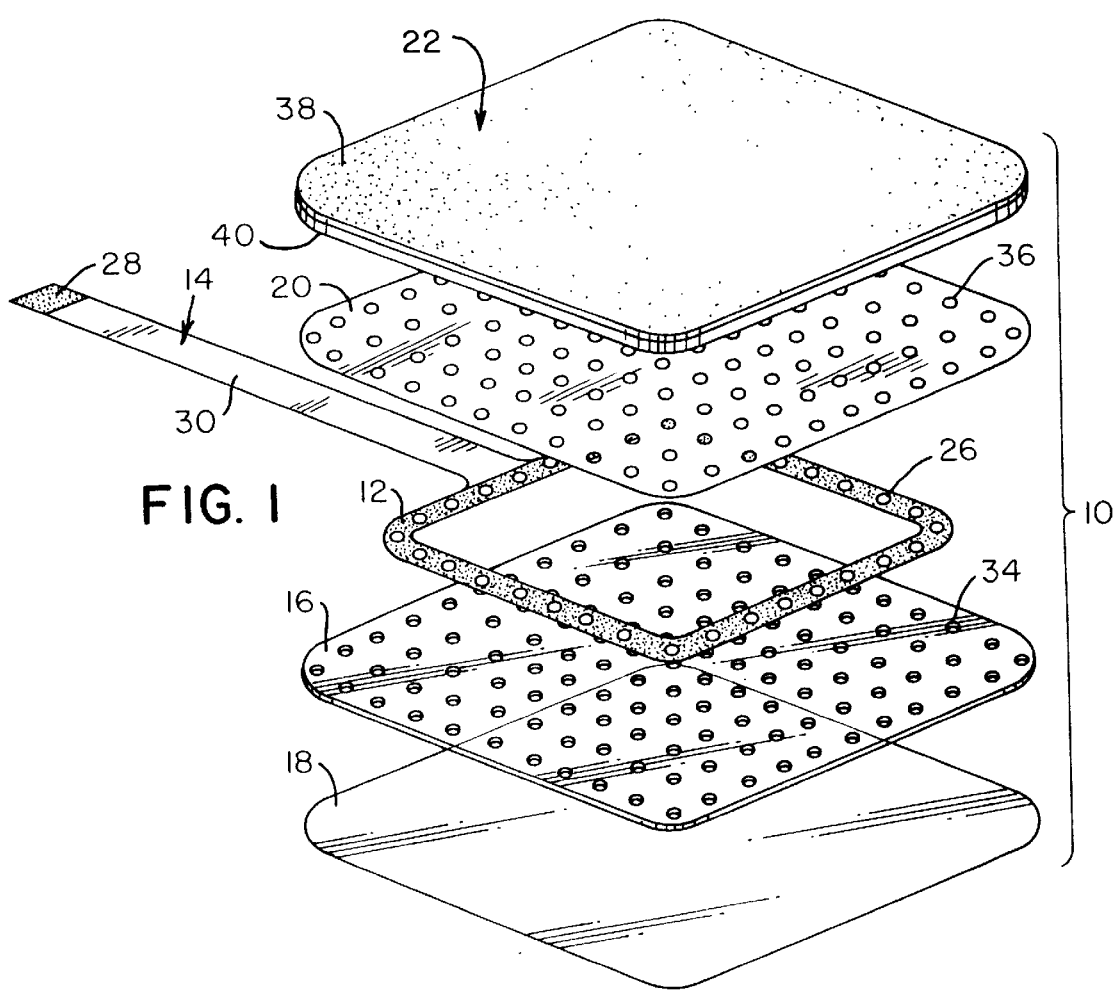
FIG. 1 is an exploded perspective view of a wound care electrode in accordance with the present invention.
Figure 2:
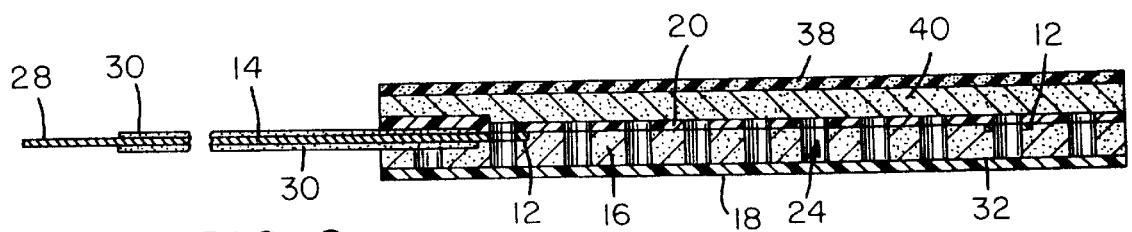
FIG. 2 is an enlarged cross-sectional view of the wound care electrode of FIG. 1.

Referring now to FIGS. 1 and 2, a wound care electrode in accordance with the present invention is shown at 10. The electrode 10 includes an electrically conductive body 12 having an integral, electrically conductive lead 14 extending therefrom. Applied to the bottom of the conductive body 12 is an electrically conductive, hydrogel layer 16 whose bottom surface is itself covered with a removable, release liner 18 during storage and prior to use. Secured to the top of the conductive body 12 is a non-conductive, separating layer 20. Atop the separating layer 20 is secured a hydrocolloid dressing 22 for absorbing wound seepage conveyed to it via apertures 24 extending through the conductive body 12, hydrogel layer 16 and separating layer 20.

The conductive body 12 is preferably formed from a thin film (approximately 0.1 mm thick) of silicone rubber or other material which has been made electrically conductive by the addition of carbon black. The conductive body 12 has a rectangular, loop-like form (measuring about 7.5 cm along each side thereof) for encircling a wound during use. Preferably, the conductive body 12 is perforated as at 26 to provide a portion of the apertures 24 in the electrode 10 after assembly of the various elements thereof.

The lead 14 extends from one side of the conductive body 12 and has a preferred length of about 11.0 cm. All but about 1.0 cm located at the free end 28 of the lead 14 is coated with a flexible, non-conductive paint 30 to prevent the inadvertent leakage of electrical current from the lead. The uncoated free end 28 of the lead 14, however, permits the electrical connection of the electrode 10 to a remote, galvanic stimulator (not shown).

The hydrogel layer 16 comprises a natural or synthetic hydrocolloid combined with a liquid hydrating agent. The hydrogel layer 16 is in the form of a stable, non-fluid gel which, although sufficiently pliant to conform to skin contours and flex when the skin moves, will not flow appreciably during storage or after being applied to the skin of a user. The hydrogel layer 16 has a tacky surface 32 which is adapted to adhere to the skin of a user and provide a reliable electrical contact therewith. When applied to the skin, body moisture, body salts and heat are absorbed into the hydrogel layer 16 thereby increasing the tackiness of surface 32.

Perforations, as at 34, extend through the hydrogel layer 16. As may best be seen in FIG. 2, these perforations are axially aligned with similar perforations 26 and 36 in the conductive body 12 and the separating layer 20 to provide the apertures 24 in the electrode 10. Preferably, the perforations 26, 34 and 36 each have diameters of about 3.0 mm, but they may be larger or smaller as desired. It should be noted that perforations 26, 34 and 36 of relatively smaller diameter advantageously tend to draw greater volumes of liquid, wound seepage away from the skin of a user and into the apertures 24 formed thereby through capillary action.

The hydrogel layer 16 is dimensioned to separate the conductive body 12 from the skin of a user and adequately adhere the electrode 10 to the skin of a user. Preferably, the hydrogel layer 16 measures about 10.0 cm by 10.0 cm. The thickness of the hydrogel layer 16, on the other hand, is about 1.0 mm.

Since the hydrogel layer 16 is subject to drying, the release liner 18 is provided on the tacky surface 32 for storage before use. The release liner 18 is preferably formed of flexible plastic, but may be formed from any other suitable material which is removable from the hydrogel layer 16 without disturbing its integrity.

The separating layer 20 provides a gap of predetermined width (about 0.5 mm which is the thickness of the separating layer 20) between the hydrogel layer 16 and the hydrocolloid dressing 22 thereby preventing the dressing from absorbing a portion of the hydrogel. The separating layer 20 also serves as a temporary support for the relatively fragile, conductive body 12 which may be secured to the separating layer prior to final assembly of the electrode 10 by means of a suitable adhesive.

The hydrocolloid dressing 22 comprises a protective upper layer 38 and an absorbent lower layer 40. The upper layer 38 is preferably a nonconductive, open-celled, plastic foam such as polyurethane or polyethylene. The lower layer 40, however, comprises a natural or synthetic hydrocolloid with a liquid hydrating agent, i.e., a hydrogel. The lower layer 40, like layer 16, is flexible and stable under normal conditions of use. In accordance with this invention, the dressing 22 has an overall thickness of about 1.5 mm with the upper layer 38 being about 0.5 mm thick.

The electrode 10 may be made with conventional equipment in a continuous production process. The film which is to form both the conductive body 12 and the lead 14 is first fed from a roll. As the film is advanced, the conductive body 12 and lead 14 are cut into the desired shape. Next, a coating of insulative paint 30 is applied to the lead 14 and an adhesive is applied to one side of the conductive body 12. Then, the sheeting that is to form the separating layer 20 is fed from a roll and brought into engagement with the side of the conductive body 12 bearing the adhesive thereby securing the conductive body to the sheeting.

Later, the liquified material which is to form the hydrogel layer 16 is deposited atop the conductive body 12 and the sheeting that is to form the separating layer 20 and allowed to harden into a gel which has good adhesion with the conductive body and sheeting. After hardening, the apertures 24 are formed through the separating layer 20, conductive body 12, and hydrogel layer 16 by means of a mechanical punch or press. To protect the tacky surface 32 of the hydrogel layer 16, the material that is to form the protective release liner 18 is fed from a roll and positioned atop the surface 32 so as to form a cover therefor.

While the hydrogel layer 16 is hardening, the foam which is to form the upper layer 38 of the hydrocolloid dressing 22 is fed from a roll. The liquid gel which is to form the lower layer 40 of the dressing 22 is then poured over the foam and thereafter allowed to partially set into gelled material which has good adhesion with the foam and any other thing brought into contact therewith. (The open-celled nature of the foam, of course, permits the liquid gel to partially flow into it and strongly bond thereto). After this operation has been completed, the exposed surface of the partially gelled material which is to form the layer 40 is brought into direct contact with the exposed surface of the future separating layer 20 thereby adhering the two elements together. The electrode 10 is then die cut to shape and is severed from the selvage of the sandwiched stock materials used in the production process.

The finished electrode 10 has an overall thickness of about 3.0 mm. Due to the thinness of the electrode 10 and the flexibility of the materials from which it is constructed, it is capable of bending to conform to the skin of a user as the user sits or moves about. When necessary, the electrode 10 may be easily inserted within a cast, splint or other orthotic device for use.

Normal use of the electrodes 10 involves cleaning, in the usual manner, a wound (surgical incision, abrasion, cut, puncture, tear, sore and the like) in the skin of a user. After cleaning, the release liner 18 is removed from an electrode 10 and its tacky surface 32 is pressed against the wound to adhere the electrode to it. Next, a second electrode 10 is applied to the skin of a user at a site remote from the first electrode. The electrodes 10 are now respectively connected to the positive and negative poles of a remote electrical current source such as a galvanic stimulator by means of alligator clip connectors (not shown) clipped to the free ends 28 of the leads 14. Finally, an electrical current, sufficient to promote the healing of the wound, is flowed through the circuit including the two electrodes 10 and the electrical current source. After use, the electrodes 10 may be easily removed from the skin of a user and conveniently discarded.

Certain areas of the human body, such as the heel, ankle and ball of the foot, are more difficult than other to bond the electrodes 10 to. Thus, to obtain a good bond, the hydrogel layer 16, separating layer 20 and hydrocolloid dressing 22 may all be provided with transverse cuts from a knife or scissors to permit the electrode 10 to better conform to the contours of the skin. In the case of nonhealing ostomy sites or other openings in the body where complete coverage by an electrode 10 is not desired, the center portion of each of the hydrogel layer 16, separating layer 20 and dressing 22 may be fully removed so that the electrode will encircle, but not cover, the opening.

The form of the conductive body 12 may be varied to increase the electrical current density to certain types of wounds. As shown in FIG. 4, the conductive body 112 may be provided with a closed circular shape for use in treating relatively small wounds. The conductive body 212 of FIG. 5, however, has plurality of arms 215 radiating from a common location in a cruciform pattern to aid in conforming the body 212 to the distal ends of the stumps of amputees. Both bodies 112 and 212 are provided with perforations 126 and 226 for the passage of wound seepage and integral leads 114 and 214 for attachment to an electrical current source. Like the lead 14, leads 114 and 214 are coated with a flexible, nonconductive paint at 130 and 230 to prevent current leakage.

While the invention has been described with a high degree of particularity, it will be appreciated by those skilled in the art that modifications may be made thereto. For this reason, it is to be understood that the present invention is not limited to the embodiments described above, but encompasses any and all embodiments within the scope of the following claims.

I claim:

1. A wound care electrode, comprising:
    a flexible, electrically conductive body having a top and a bottom;
    an electrically conductive gel layer secured to the bottom of said electrically conductive body for releasably coupling said electrically conductive body with the skin of a user, said electrically conductive gel layer having a top and a bottom;
    a flexible, nonconductive, separating layer secured to the top of said electrically conductive body, said separating layer having a top and a bottom;
    a flexible, absorbent dressing secured to the top of said separating layer; and,
    said electrically conductive body, said electrically conductive gel layer, and said separating layer having axially aligned perforations for conveying seepage from the skin of a user to said absorbent dressing.

2. The wound care electrode according to claim 1 wherein said electrically conductive body is a closed loop adapted to encircle a wound in the skin of a user.

3. The wound care electrode according to claim 1 wherein said electrically conductive body includes a plurality of electrically conductive arms radiating from a common location.

4. The wound care electrode according to claim 1 further comprising a flexible, electrically conductive lead integral with said electrically conductive body.

5. The wound care electrode according to claim 4 wherein said electrically conductive body and said lead comprise a piece of carbon carrying film.

6. The wound care electrode according to claim 5 further comprising a flexible, nonconductive coating on said lead.

7. The wound care electrode according to claim 1 wherein said absorbent dressing comprises a porous, nonconductive material supporting a hydrogel layer, and said hydrogel layer abutting said separating layer.

8. The wound care electrode according to claim 1 further comprising a protective release liner releasably secured to the bottom of said electrically conductive gel layer.

9. A wound care electrode, comprising:
    an electrically conductive body having a bottom and a top;
    an electrically conductive lead integrally formed with said electrically conductive body, said electrically conductive lead having a free end remote from said electrically conductive body;
    said electrically conductive body and said electrically conductive lead being formed from a flexible, polymeric film;
    a flexible, nonconductive coating covering said electrically conductive lead from said electrically conductive body to a point proximate said free end thereof;
    an electrically conductive gel layer secured to the bottom of said electrically conductive body for releasably coupling said electrically conductive body with the skin of a user, said electrically conductive gel layer having a top and a bottom;
    a flexible, nonconductive, separating layer secured to the top of said electrically conductive body, said separating layer having a top and a bottom;
    a flexible, absorbent dressing secured to the top of said separating layer; and,
    said electrically conductive body, said electrically conductive gel layer, and said separating layer having axially aligned perforations for conveying seepage from the skin of a user to said absorbent dressing.

10. The wound care electrode according to claim 9 wherein said electrically conductive body is a closed loop adapted to encircle a wound in the skin of a user.

11. The wound care electrode according to claim 9 wherein said electrically conductive body includes a plurality of electrically conductive arms radiating from a common location.

12. The wound care electrode according to claim 9 wherein said absorbent dressing comprises a porous, nonconductive material supporting a hydrogel layer, and said hydrogel layer abutting said separating layer.

13. The wound care electrode according to claim 9 further comprising a protective release liner releasably secured to the bottom of said electrically conductive gel layer.

14. A wound care electrode, comprising:
    an electrically conductive body having a top and a bottom;
    an electrically conductive lead integrally formed with said electrically conductive body, said electrically conductive lead having a free end remote from said electrically conductive body;
    said electrically conductive body and said electrically conductive lead being formed from a flexible, polymeric film made electrically conductive by the addition of carbon black;
    a flexible, nonconductive coating covering said electrically conductive lead from said electrically conductive body to a point adjacent said free end thereof;
    a first hydrogel layer secured to the bottom of said electrically conductive body for releasably coupling said electrically conductive body with the skin of a user, said first hydrogel layer having a top and a bottom;
    a flexible, nonconductive, polymeric, separating layer secured to the top of said electrically conductive body, said separating layer having a top and a bottom;
    a second hydrogel layer secured to the top of said separating layer, said second hydrogel layer having a top and bottom;
    a porous, nonconductive, polymeric foam secured to the top of said second hydrogel layer; and,
    said electrically conductive body, said first hydrogel layer, and said separating layer having axially aligned perforations defining apertures for conveying seepage from the skin of a user to said second hydrogel layer and said polymeric foam.

15. The wound care electrode according to claim 14 further comprising a protective release liner releasably secured to the bottom of said first hydrogel layer.

16. The wound care electrode according to claim 14 wherein said electrically conductive body is a closed loop adapted to encircle a wound in the skin of a user.

17. The wound care electrode according to claim 14 wherein said electrically conductive body includes a plurality of electrically conductive arms radiating from a common location.

* * * * *